United States Patent
Fan et al.

(10) Patent No.: US 11,314,327 B2
(45) Date of Patent: Apr. 26, 2022

(54) HEAD MOUNTED DISPLAY AND CONTROL METHOD THEREOF

(71) Applicant: HTC Corporation, Taoyuan (TW)

(72) Inventors: Fu-Cheng Fan, Taoyuan (TW); Chung-Jung Chen, Taoyuan (TW)

(73) Assignee: HTC Corporation, Taoyuan (TW)

( * ) Notice: Subject to any disclaimer, the term of this patent is extended or adjusted under 35 U.S.C. 154(b) by 0 days.

(21) Appl. No.: 17/149,742

(22) Filed: Jan. 15, 2021

(65) Prior Publication Data

US 2021/0333871 A1 Oct. 28, 2021

Related U.S. Application Data

(60) Provisional application No. 63/013,554, filed on Apr. 22, 2020.

(51) Int. Cl.
*G06F 3/01* (2006.01)
*G09G 5/38* (2006.01)
*G09G 5/37* (2006.01)

(52) U.S. Cl.
CPC ............... *G06F 3/013* (2013.01); *G09G 5/37* (2013.01); *G09G 5/38* (2013.01); *G06F 3/015* (2013.01); *G09G 2320/0693* (2013.01); *G09G 2340/0464* (2013.01); *G09G 2354/00* (2013.01)

(58) Field of Classification Search
CPC ...................................................... G06F 3/013
See application file for complete search history.

(56) References Cited

U.S. PATENT DOCUMENTS

| | | | |
|---|---|---|---|
| 2013/0031511 A1* | 1/2013 | Adachi | G06F 3/0481 715/825 |
| 2017/0115729 A1* | 4/2017 | Han | G06F 3/0346 |
| 2018/0292896 A1 | 10/2018 | Hicks et al. | |
| 2021/0165484 A1* | 6/2021 | Suguhara | H04N 13/268 |

FOREIGN PATENT DOCUMENTS

| | | |
|---|---|---|
| CN | 105718046 | 6/2016 |
| TW | 201942646 | 11/2019 |
| TW | 202004421 | 1/2020 |

OTHER PUBLICATIONS

"Office Action of Taiwan Counterpart Application", dated Nov. 9, 2021, p. 1-p. 15.

* cited by examiner

*Primary Examiner* — Gustavo Polo
(74) *Attorney, Agent, or Firm* — JCIPRNET

(57) ABSTRACT

A head mounted display and a control method thereof are provided. The control method includes the following. An eye-tracking operation is activated to obtain a gazing direction of a user. At least one setting position is set on a display frame, and the at least one setting position serves to set at least one static object. Whether to display or hide the static object is determined according to the setting position and the gazing direction.

12 Claims, 4 Drawing Sheets

HEAD MOUNTED DISPLAY AND CONTROL METHOD THEREOF

CROSS-REFERENCE TO RELATED APPLICATION

This application claims the priority benefit of U.S. Provisional Application No. 63/013,554, filed on Apr. 22, 2020. The entirety of the above-mentioned patent application is hereby incorporated by reference herein and made a part of this specification.

BACKGROUND

Technical Field

The disclosure relates to a head mounted display and a control method thereof, and more particularly to a head mounted display and a control method thereof that can reduce a cybersickness phenomenon.

Description of Related Art

With the progress in electronic technology, people's demand for display quality has greatly increased. In view of this, a head mounted display that can provide a virtual reality/augmented reality has been proposed.

With the provided virtual reality/augmented reality display effects, the head mounted display allows a user to visually generate a feeling of speed of moving in space. However, the semicircular canal system in the inner ears of the user does not actually sense an effective movement of the user. The conflict between visual and somatosensory sensations may result in the so-called cybersickness phenomenon of the user. In the present technical field, how to effectively reduce the cybersickness phenomenon certainly poses an issue for the designers of head mounted displays to work on.

SUMMARY

The disclosure provides a head mounted display and a control method thereof, which can improve comfort of use of a user.

The control method of the head mounted display of the disclosure includes the following. An eye-tracking operation is activated to obtain a gazing direction of a user. At least one setting position is set on a display frame, and the at least one setting position serves to set at least one static object. Whether to display or hide the static object is determined according to the setting position and the gazing direction.

The head mounted display of the disclosure includes an eye-tracking device, a display device, and a controller. The eye-tracking device performs an eye-tracking operation. The display device generates a display frame and at least one static object. The controller serves to perform the control method.

Based on the above, the head mounted display of the disclosure can appropriately display one or more static objects outside a specific field-of-view of a user according to the gazing direction of the user. By displaying the static object, the possibility of the user experiencing the cybersickness phenomenon can be reduced, and an immersive feeling of the user enjoying the virtual reality/augmented reality can be maintained. The gazing direction of the user of the disclosure may also be obtained through a method such as electroencephalography (EEG), electromyography (EMG), and the like.

DESCRIPTION OF THE EMBODIMENTS

Figure 1:
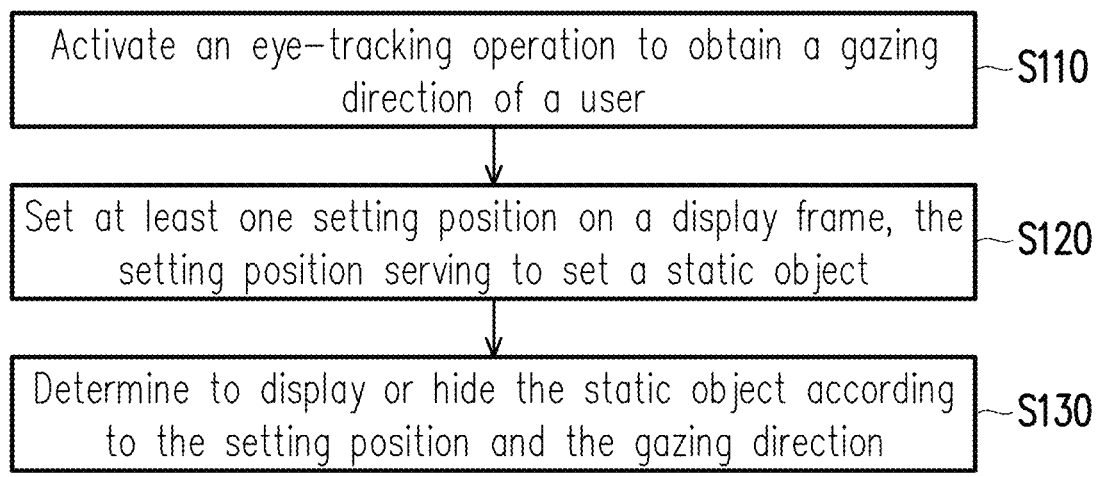
FIG. 1 shows a flowchart of a control method of a head mounted display according to an embodiment of the disclosure.

Referring to FIG. 1, FIG. 1 shows a flowchart of a control method of a head mounted display according to an embodiment of the disclosure. In step S110, the head mounted display may activate an eye-tracking operation to obtain a gazing direction of a user. Through the eye-tracking operation, the head mounted display may recognize an eye position of the user, and the head mounted display may also recognize the gazing direction of the user. In addition, in step S120, the head mounted display may set one or more setting positions on a display frame. In the embodiment, the setting position serves to display a static object. Next, in step S130, the head mounted display may determine to display or hide the corresponding static object according to the setting position and the gazing direction.

Figure 2:
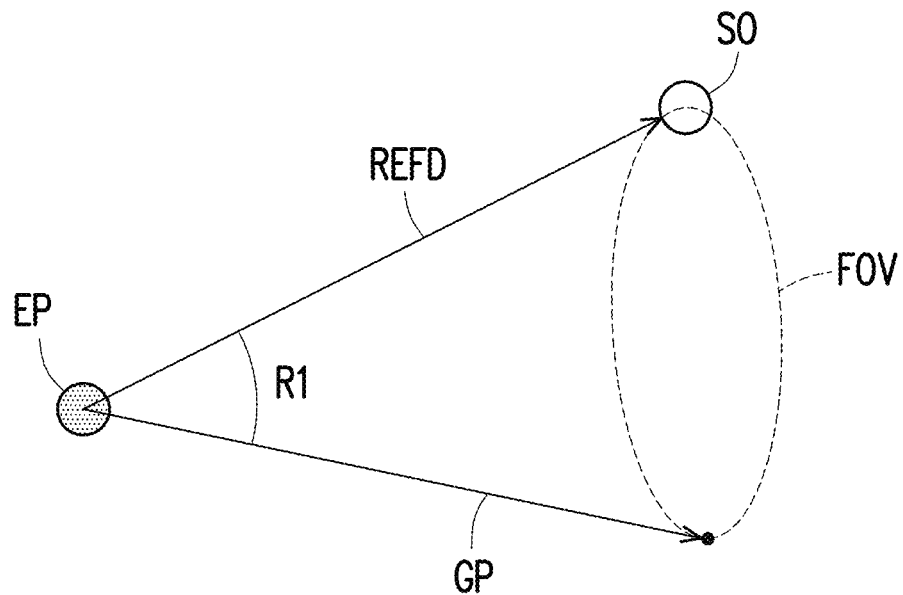
FIG. 2 shows a schematic view of a method of determining a field-of-view according to an embodiment of the disclosure.

For details, referring to both FIG. 1 and FIG. 2, FIG. 2 shows a schematic view of a method of determining a field-of-view according to an embodiment of the disclosure. In the embodiment, the head mounted display generates a field-of-view FOV based on the setting position serving to display a static object SO and a gazing direction GP of the user (the field-of-view FOV here is like a cone having a vector in the gazing direction GP as a center, and is called the field-of-view easily perceivable by the human eye). The head mounted display determines to display the static object SO at the setting position or hide the static object SO at the setting position according to a size of the field-of-view.

Specifically, in the embodiment, the eye position EP of the user may be obtained through the eye-tracking operation. A reference direction REFD is generated according to the eye position EP of the user and the setting position SO on the display frame. The head mounted display may further calculate an included angle R1 between the reference direction REFD and the gazing direction GP of the user. In the embodiment, the head mounted display may adopt the included angle R1 less than 180 degrees between the reference direction REFD and the gazing direction GP of the user.

The head mounted display may calculate whether the included angle R1 is less than a predetermined value (e.g., a first predetermined value) as a basis for whether to display the static object SO. For example, when the included angle R1 between the reference direction REFD and the gazing direction GP of the user is less than the first predetermined value, the user may visually perceive an existence of the static object, and since the position of the static object is only determined by such method and has nothing to do with a current 3D spatial position, a current 3D spatial orientation, and a current display frame of the head mounted display of the user, the static object may attract attention of the user to the static object, and destroy a highly immersive feeling of a virtual world that the head mounted display intends to create. The head mounted display may hide the static object SO at the setting position, so as to prevent a display image of the static object SO from being perceived by the user and destroying the immersive feeling of the virtual world.

On the other hand, the head mounted display may further calculate whether the included angle R1 is greater than another predetermined value (e.g., a second predetermined value) as a basis for whether to display the static object SO. When the included angle R1 between the reference direction REFD and the gazing direction GP of the user is greater than or equal to the second predetermined value, the static object SO has not yet entered a main visual perception area of the user. The head mounted display may display the static object SO at the setting position. Through the display of the static object SO, a signal that is more consistent with a vestibular system at the moment may be added to visual information during the user's image experience in virtual reality/augmented reality, so that when the human brain processes and integrates all the signals from each sense, sensory mismatches between current spatial positions respectively obtained from a vestibular system and a vision system are particularly reduced. As a result, a possibility of cybersickness is reduced. More specifically, when using the virtual head mounted display, if the user has no body movement and is given frames of flying forward, the vestibular system perceives a static state, but the vision system perceives a flying state. Such difference between the two systems is inconsistent with prior experiences memorized in the human brain. As a result, a phenomenon similar to poisoning may arise, which may lead to physiological reactions such as vomiting and nausea.

The first threshold value and the second threshold value are not particularly related in terms of size, and the first threshold value and the second threshold value may be equal or not equal to each other.

In addition, in the embodiment, the number of the static object SO in a display frame may be one or more and is not particularly limited. In addition, there is no predetermined setting rule for the setting positions of the multiple static objects SO on the display frame. For example, the setting positions of the static objects SO may be evenly distributed on the display frame as an array, or be set to be unevenly distributed on the display frame. In addition, the individual static object SO may be in the size of a pixel or in a size larger than a pixel. During a display period, the position of the static object SO on the display frame does not change with a movement or a rotation of the head mounted display in a 3D space.

That is, a viewing angle of the user observing the static object SO is approximately $\frac{1}{15}$ degrees. In such a state, the static object SO may reduce the possibility of cybersickness in a display state.

A color and a brightness of the static object SO may be set according to a background image of the display frame at the corresponding setting position. The color and the brightness of the static object SO may be set by calculating a color average value and a brightness average value of N pixels in the display frame that are at the setting position, and N may be any positive integer.

In addition, the static objects SO on a display frame may have a same depth-of-focus. Moreover, the static objects SO on planes of different focal lengths may have a same size. Besides that, the static object SO is not performed as a centralized rendering process is performed. Moreover, corresponding to an eye (left eye or right eye) of the user, the setting position of the static object SO does not change.

Figure 3A:
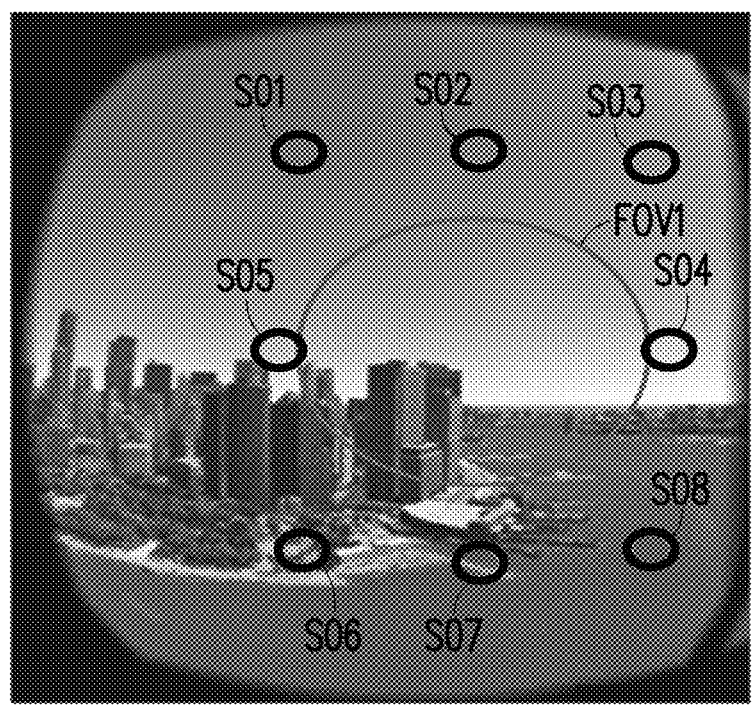
FIG. 3A and FIG. 3B show schematic views of operations according to a control method of a head mounted display according to another embodiment of the disclosure.
Figure 3B:
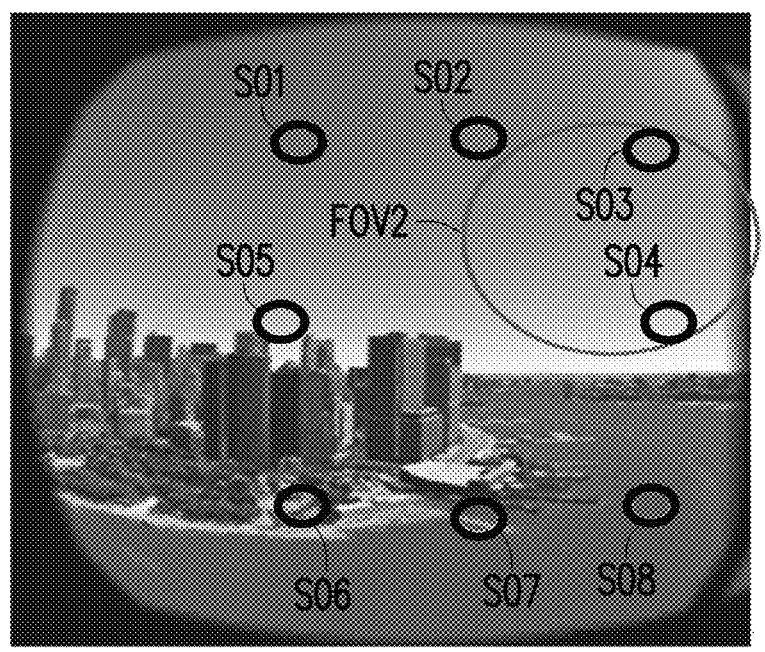

Referring to FIG. 3A and FIG. 3B for the following, FIG. 3A and FIG. 3B show schematic views of operations according to a control method of a head mounted display according to another embodiment of the disclosure. In FIG. 3A and FIG. 3B, the head mounted display sets multiple setting positions on the display frame, and the setting positions respectively serve to display static objects SO1 to SO8. In FIG. 3A, the head mounted display activates the eye-tracking operation and obtains the gazing direction of the eye of the user. The head mounted display further calculates a reference field-of-view RFOV1 according to the gazing direction of the eye of the user and the predetermined threshold value. The head mounted display finds the static objects in the reference field-of-view RFOV1 according to the reference field-of-view RFOV1, and hides the static objects inside the reference field-of-view RFOV1. In contrast, the static objects outside the reference field-of-view RFOV1 may be displayed.

In the embodiment, when the static object is included in the reference field-of-view RFOV1, the included angle between the setting position of the static object, the eye position, and the gazing direction of the user is less than the predetermined threshold value. Therefore, the corresponding static object should be hidden.

In addition, in FIG. 3B, the head mounted display further calculates another reference field-of-view RFOV2 according to another gazing direction of the eye of the user and the predetermined threshold value. The head mounted display finds the static objects (e.g., the static object SO3 and the static object SO4) in the reference field-of-view RFOV2 according to the reference field-of-view RFOV1, and hides the static object SO3 and the static object SO4 in the reference field-of-view RFOV2. At the same time, the other static objects SO1 to SO2 and SO5 to SO8 remain displayed.

Figure 4:
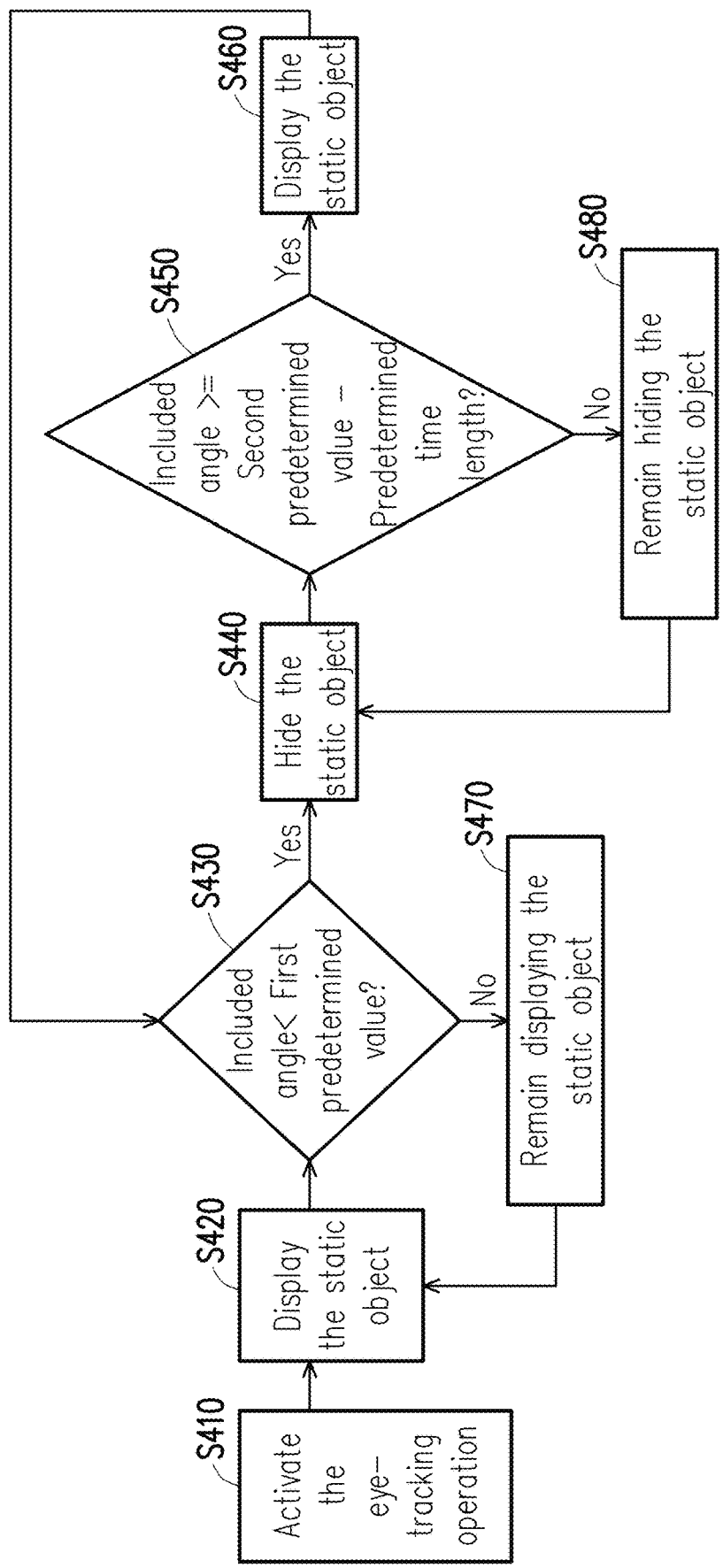
FIG. 4 shows a schematic view of a control method of a head mounted display according to another embodiment of the disclosure.

Referring to FIG. 4 for the following, FIG. 4 shows a schematic view of a control method of a head mounted display according to another embodiment of the disclosure. In step S410, the head mounted display activates the eye-tracking operation, and the eye-tracking operation serves to determine the eye position and the gazing direction of the user. Next, in step S420, the head mounted display sets one or more setting positions on the display frame, and performs a display operation of the static object according to the setting position. In the embodiment, the size of the static object may be set in advance, and the color and the brightness of the static object may be determined according to the current background image of the display frame that is at the setting position. That is to say, the colors and the brightness of the static objects may be independently set, and are not necessarily the same. A controller may refer to a red, green, and blue (RGB) grayscale of the pixel of the static object currently to be displayed, and an average grayscale value X of the area plus/minus a predetermined parameter P becomes X'=X+/−P, where X' is a new RGB grayscale setting value of the pixel, and becomes a setting value of the color and the brightness of the static object.

In step S430, the head mounted display may calculate the included angle between the eye position, the reference direction of the setting position, and the gazing direction for each static object, and determine whether the included angle is less than the first predetermined value. If the corresponding included angle of the determined static object is less than the first threshold value, step S440 is performed to hide the static object. Alternatively, if the corresponding included angle of the determined static object is not less than the first threshold value, step S470 is performed to remain displaying the static object.

Following step S440, in step S450, the head mounted display may target the hidden static object in the display frame, when the corresponding included angle of the determined static object is greater than or equal to the second predetermined threshold value, and the state remains for a predetermined time length, the head mounted display may change the originally hidden static object to be displayed (step S460). Alternatively, if the determination result of step S450 is No, the head mounted display remains hiding the static subject. The first predetermined value and the second predetermined value may also be dynamically adjusted by calculating the difference between a current dynamic change degree of the frame and a current dynamic change degree of the head mounted display.

It is worth mentioning that in step S450, to avoid the phenomenon that the included angle temporarily becomes greater than or equal to the second predetermined threshold value because a sightline of the user rapidly moves so that the static object needs to be quickly hidden after being displayed, which leads to an afterimage phenomenon, the embodiment sets the predetermined time length. After it is determined that the corresponding included angle of the static object has been greater than or equal to the second predetermined threshold value for the predetermined time length, step S460 is performed to display the static object, and the display quality can be maintained.

Figure 5:
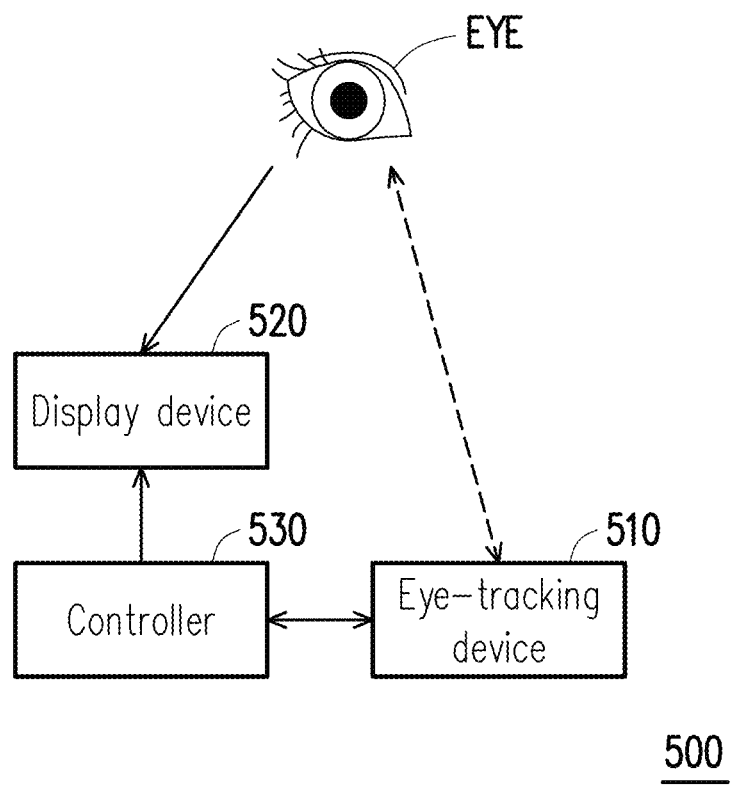
FIG. 5 shows a schematic view of a head mounted display according to an embodiment of the disclosure.

Referring to FIG. 5 for the following, FIG. 5 is a schematic view of a head mounted display according to an embodiment of the disclosure. A head mounted display 500 includes an eye-tracking device 510, a controller 530, and a display device 520. The controller 530 is coupled to the eye-tracking device 510 and the display device 520. In the embodiment, the eye-tracking device 510 serves to perform the eye-tracking operation to determine the position and the gazing direction of an eye EYE of the user. The eye-tracking operation may also be obtained by calculating the gazing direction of the other eye measured by the other eye-tracking device, a pupil distance between two eyes, and a spatiotemporal positioning state of the head mounted display. The display device 520 serves to provide the display frame, and display one or more static objects in the display frame according to the setting position.

In the embodiment, the controller 530 serves to perform the operation procedure of the control methods as shown in FIG. 1 and FIG. 4, and serves to determine whether each static object is displayed or hidden. Through providing the static object on the display frame, the head mounted display 500 of the embodiment reduces the possibility of cybersickness during the process in which the user experiences the virtual reality/augmented reality while maintaining the immersive feeling experienced in the virtual world.

In the embodiment, the display device 520 may be any flat or non-flat display device known to persons with ordinary knowledge in the art, and there is no specific limitation. The eye-tracking device 510 may have a light emitting diode, a camera, and an eye-tracking calculator. The light emitting diode serves to project a light beam to the eye EYE of the user and generate a light spot on the eye EYE of the user, and the camera serves to capture an image of the eye EYE. The eye-tracking device 510 may calculate the position and the gazing direction of the eye EYE through a distribution state of image light spots on the eye EYE. In the embodiment, the position and the gazing direction of the eye EYE may also be calculated and obtained by the controller 530, and the disclosure is not particularly limited in this regard.

Of course, the aforementioned embodiment of the eye-tracking device 510 is only an example for illustration, and any eye-tracking technology known to persons skilled in the art may be used in the embodiment, and the disclosure is not particularly limited in this regard.

In addition to using the eye-tracking device to obtain the sightline of the user, an algorithm may also be used to calculate and analyze frame contents of several previous display frames to determine a most possible sightline position of the user. The frame contents include, for example, a movement of a main object, a laser pointer position of a virtual reality (VR) handle, a position where a loudest volume is made, a position where a new object appears, a position of a human finger in a frame within a VR space, etc., or a trained model by using above extracted features.

In addition to using the sightline of the user to determine whether to display the static object, a rotating or moving state, such as a magnitude and a direction (XYZ) of an acceleration in an axial direction, of the head mounted display obtained by a gyroscope, an accelerometer, a magnetometer, or other spatial positioning tracking technology of the head mounted display may also be used. Here, an individual index of current dynamic spatial positioning of the head mounted display may be comprehensively calculated in real time. When the dynamic spatial positioning index is greater than a predetermined threshold value K, some or all static objects are displayed, and when less than the predetermined threshold value K, some or all static objects are hidden. The dynamic spatial positioning index may also serve to determine ON or OFF of a power of an eye module. When the dynamic spatial positioning index is greater than a predetermined threshold value P, the power of the eye module is turned off, or a frame rate is reduced, or a sleep mode is turned on, so as to reduce power consumption. The dynamic spatial positioning index may also serve to dynamically adjust the size (the number of pixels occupied), the color, and the like of the static object. It may be that the stronger the dynamic spatial positioning index, the larger the size of the static objects, the greater the color contrast, or the greater the number of the static objects. Comparatively, when the head mounted display is static, the smaller the size of the static objects, the smaller the color contrast, or the smaller the number of the static objects.

Regarding the controller 530, the controller 530 may be a processor having a computing capability. Or, the controller 530 may be a hardware circuit designed in a hardware description language (HDL) or any other digital circuit design method known to persons with ordinary knowledge in the art, and implemented through in a way such as a field programmable gate array (FPGA), a complex programmable logic device (CPLD), or an application-specific integrated circuit (ASIC). The controller 530 may also be remotely located and obtain information of an eye-tracking module through a common wireless transmission method (e.g., WIFI and 5G), and the information includes but is not limited to the sightline of the human eye, the eye spatial position, etc. The controller, the display device, and the eye-tracking module may also be integrated into a device. The display device is built with a light sensing array to capture eye image information, and a built-in controller or logic circuit built in the display device is used to calculate the sightline of the human eye, determine whether to display the static object, and display the static object, and a lighting part for eye tracking may be provided by a backlight of a liquid crystal display (LCD) itself, an organic and inorganic self-luminous light, and the like.

The disclosure further includes a calibration method. The calibration method may be actively loaded by a VR application, or be selected and executed by the user in a setting module after the user wears the head mounted display. The calibration method mainly serves to adjust the optimal position of the static object in the field-of-view of the human eye, so as to optimally reduce cybersickness. Since the size of the field-of-view seen by each person after wearing a head mounted display is different, the optimal position, size, shape, and color of the static object may also be different for different people. In a first stage, the field-of-view of the user is measured. In this stage, different numbers may be displayed at different viewing angles, and a current maximum viewing angle of the user is measured through the user holding the VR handle to point and click, giving a voice response, subjected to eye-tracking, brain waves, or using other human-machine interface measurements, and thereby sets the position of the static object. In a second stage, frames of the static objects of different positions, sizes, shapes and colors are played. The frames include a frame of one of the left eye and the right eye having no static object; after a start, the user is asked to look straight at a center reference point, and the user is asked to answer whether they can visually perceive the existence of the static object. The above calibration method is used to find a static object parameter setting of the user able to achieve the optimal effect of reducing cybersickness while maintaining the optimal VR immersive feeling experience. The static object parameter setting of the user may be stored and automatically loaded the next time the head mounted display is activated. The calibration method may be combined with an eye-tracking calibration process after being properly designed. Another quick method is to directly use relevant position parameters of the eye of the user and the head mounted display in the virtual space, an age of the user, a gender of the user, and whether the user wears glasses to calculate the viewing angle, so as to calculate the viewing angle and a favorable relative setting of the static object.

In summary of the above, the head mounted display of the disclosure displays the static objects at one or more setting positions in the display frame. Through the display of the static objects, the possibility of cybersickness happening when the user is experiencing virtual reality/augmented reality may be reduced. In addition, the head mounted display of the disclosure may determine to hide or display each static object according to the gazing direction of the user, and cybersickness is reduced on a premise of maintaining the display quality.

What is claimed is:

1. A control method of a head mounted display, comprising:
    activating an eye-tracking operation to obtain a gazing direction of a user;
    setting at least one setting position in a display frame, wherein the at least one setting position serves to set at least one static object;
    generating at least one reference direction according to an eye position and the at least one setting position;
    calculating an included angle between the at least one reference direction and the gazing direction to obtain at least one field-of-view; and
    determining to display the at least one static object when the at least one static object is outside the at least one field-of-view, and determining to hide the at least one static object when the at least one static object is inside the at least one field-of-view.

2. The control method according to claim 1, wherein a step of determining to display the at least one static object when the at least one static object is outside the at least one field-of-view, and determining to hide the at least one static object when the at least one static object is inside the at least one field-of-view-comprises:
    determining to display or hide the at least one static object according to a size of the at least one field-of-view.

3. The control method according to claim 2, wherein the included angle between the at least one reference direction and the gazing direction is less than 180 degrees.

4. The control method according to claim 3, wherein a step of determining to display the at least one static object when the at least one static object is outside the at least one field-of-view, and determining to hide the at least one static object when the at least one static object is inside the at least one field-of-view comprises:
    hiding the at least one static object when the included angle between the at least one reference direction and the gazing direction is less than a first predetermined value; and
    changing the at least one static object to be displayed when the at least one static object is hidden and the included angle between the at least one reference direction and the gazing direction becomes greater than or equal to a second predetermined value and remains for a predetermined time length.

5. The control method according to claim 4, wherein the predetermined time length is between 1/60 seconds and 5 seconds.

6. The control method according to claim 4, wherein the at least one static object comprises one or more than one pixel; wherein during a display period, a position of the at least one static object in the display frame does not change with a movement or a rotation of the head mounted display in a three dimensional space.

7. A head mounted display, comprising:
    an eye-tracking device performing an eye-tracking operation;
    a display device generating a display frame and at least one static object; and
    a controller, configured to:
        activate the eye-tracking operation of the eye-tracking device to obtain a gazing direction of a user;
        set at least one setting position on the display frame, wherein the at least one setting position serves to set at least one static object;
        generate at least one reference direction according to an eye position and the at least one setting position;
        calculate an included angle between the at least one reference direction and the gazing direction to obtain at least one field-of-view; and
        control the display device to display the at least one static object when the at least one static object is outside the at least one field-of-view, and to hide the at least one static object when the at least one static object is inside the at least one field-of-view,
    wherein the eye-tracking operation is obtained by calculating a gazing direction of the other eye measured by the eye-tracking device, a pupil distance between two eyes, and a spatiotemporal positioning state of the head mounted display.

8. The head mounted display according to claim 7, wherein the controller is configured to:

control the display device to display or hide the at least one static object according to a size of the at least one field-of-view.

9. The head mounted display according to claim 7, wherein
the included angle between the at least one reference direction and the gazing direction is less than 180 degrees.

10. The head mounted display according to claim 7, wherein the controller is configured to:
hide the at least one static object when the included angle between the at least one reference direction and the gazing direction is less than a first predetermined value; and
change the at least one static object to be displayed when the at least one static object is hidden and the included angle between the at least one reference direction and the gazing direction becomes greater than or equal to a second predetermined value and remains for a predetermined time length, wherein the first predetermined value and the second predetermined value is dynamically adjustable by calculating a difference between a current dynamic change degree of a frame and a current dynamic change degree of the head mounted display.

11. A calibration method for a head mounted display, comprising:
generating at least one reference direction according to an eye position of a user and at least one setting position in a display frame, and calculating an included angle between the at least one reference direction and the gazing direction to measure a field-of-view of the user, obtaining a current maximum field-of-view of the user through one of a plurality of methods performed by the user, and thereby setting a position of a static object, comprising determining to display the static object when the static object is outside the field-of-view, and determining to hide the static object when the static object is inside the field-of-view, wherein the at least one setting position serves to set at least one static object; and
playing a plurality of frames with different positions, sizes, shapes, and colors of static objects, wherein after a start, the user is asked to look straight at a central reference point, and the user is asked to answer whether an existence of the static object is visually perceived.

12. The calibration method according to claim 11, wherein the plurality of methods performed by the user comprise: holding a virtual reality handle to point and click, voice response, eye-tracking, brain waves, and other human-machine interface measurements.

* * * * *